(12) United States Patent
Mishima et al.

(10) Patent No.: US 6,685,688 B2
(45) Date of Patent: Feb. 3, 2004

(54) DISPOSABLE DIAPER WITH SIDE CROTCH REGIONS AND WAIST REGION HAVING AT LEAST ONE DIFFERENT DIRECTION OF STRETCHABILITY

(75) Inventors: Yoshitaka Mishima, Kagawa-ken (JP); Yasushi Sayama, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 36 days.

(21) Appl. No.: 10/183,233

(22) Filed: Jun. 26, 2002

(65) Prior Publication Data
US 2002/0161348 A1 Oct. 31, 2002

Related U.S. Application Data

(62) Division of application No. 09/608,701, filed on Jun. 30, 2001, now Pat. No. 6,436,083.

(30) Foreign Application Priority Data

Jun. 30, 1999 (JP) .......................................... 11-186660

(51) Int. Cl.⁷ ................................................ A61F 13/15
(52) U.S. Cl. ................................................ 604/385.22
(58) Field of Search ..................... 604/385.01, 385.22, 604/385.24, 385.27, 385.16

(56) References Cited

U.S. PATENT DOCUMENTS

| | | |
|---|---|---|
| 3,150,663 A | 9/1964 | Combs |
| 3,658,064 A | 4/1972 | Pociluyko |
| 4,500,316 A | 2/1985 | Damico |
| 4,990,147 A | 2/1991 | Freeland |
| 5,080,658 A | 1/1992 | Igaue et al. |
| 5,749,866 A | 5/1998 | Roe et al. |
| 5,931,826 A | 8/1999 | Faulks et al. |
| 5,993,433 A | 11/1999 | St. Louis et al. |
| 6,123,694 A | 9/2000 | Pieniak et al. |
| 6,126,648 A | 10/2000 | Keck et al. |
| 6,159,190 A | 12/2000 | Tanaka et al. |
| 6,186,996 B1 | 2/2001 | Martin |
| 6,264,642 B1 | 7/2001 | Kuen et al. |
| 6,280,428 B1 | 8/2001 | Lash et al. |
| 6,319,239 B1 | 11/2001 | Daniels et al. |
| 6,436,083 B1 * | 8/2002 | Mishima et al. ....... 604/385.24 |
| 2001/0016723 A1 | 8/2001 | Sayama et al. |
| 2001/0039408 A1 | 11/2001 | Tanji et al. |
| 2002/0002358 A1 | 1/2002 | Durrance et al. |
| 2002/0007172 A1 | 1/2002 | Takei et al. |
| 2002/0045879 A1 | 4/2002 | Karami |
| 2003/0125690 A1 * | 7/2003 | Hermansson et al. .. 604/385.01 |

FOREIGN PATENT DOCUMENTS

WO    WO 99/00095    1/1999

* cited by examiner

Primary Examiner—Weilun Lo
Assistant Examiner—Michael G. Bogart
(74) Attorney, Agent, or Firm—Butzel Long

(57) ABSTRACT

Here is disclosed a disposable diaper improved to be easily put on the wearer. Top- and backsheets in front and rear waist regions of the diaper includes the top- and backsheets that have an elastic stretchability transversely of the diaper, and transversely opposite side edges of the diaper includes top- and backsheets intended to surround the wearer's legs having elastic stretchability longitudinally and transversely of the diaper.

1 Claim, 4 Drawing Sheets

DISPOSABLE DIAPER WITH SIDE CROTCH REGIONS AND WAIST REGION HAVING AT LEAST ONE DIFFERENT DIRECTION OF STRETCHABILITY

This is a Divisional of U.S. patent application Ser. No. 09/608,701, filed on June 30, 2000 now U.S. Pat. No. 6,436,083 B1.

BACKGROUND OF THE INVENTION

This invention relates to a disposable diaper for absorbing and containing body wastes.

It is well known to use an elastically non-stretchable nonwoven fabric or a plastic film as stock materials for top- and backsheets of a disposable diaper and to provide the diaper along peripheral edges of the waist-opening and the leg-openings with elastic members secured under an appropriate tension to the diaper so that gathers may be formed along these peripheral edges and as the elastic members contract and thereby ensure a good fit of the diaper around the waist and the legs of the wearer.

The diaper of prior art is normally in its shrinked state under contraction of the elastic members and immediately before the diaper is put on the wearer, much time and trouble are required to stretch the gathers so that the waist-opening as well as the leg-openings may be sufficiently widened to facilitate the diaper to be put on the wearer. The diaper of prior art is inconvenient also in that the diaper put on the wearer is not necessarily able to follow complex movements and therefore apt to slip down or to be twisted. This is for the reason that the diaper is stretchable only in the direction along which the elastic members extend.

SUMMARY OF THE INVENTION

It is an object of this invention to provide a disposable diaper improved so that time and trouble to stretch the gathers otherwise taken to put the diaper on the wearer may be eliminated and the diaper may follow a movement of the wearer as closely as possible.

According to this invention, there is provided a disposable diaper comprising a topsheet intended to come in contact with the wearer's skin, a backsheet intended to come in contact with the wearer's garment and an absorbent core disposed between the topsheet and the backsheet wherein, the diaper has a front waist region, a rear waist region and a crotch region extending between the waist regions so that transversely opposite side edges of the crotch region surround the wearer's legs, wherein:

the topsheet and the backsheet in the front and rear waist regions are elastically stretchable in a transverse direction of the diaper while the topsheet and the backsheet at the transversely opposite side edges of the crotch region are elastically stretchable in a longitudinal direction of the diaper and in the transverse direction and the topsheet and the backsheet in the remaining regions are elastically stretchable at least in the transverse direction.

The disposable diaper according to this invention has no gathers and facilitates the diaper to be put on the wearer. The diaper according to this invention does not obstruct a movement of the wearer's legs and crotch region because the regions around the legs as well as the crotch region of the diaper are elastically stretchable longitudinally and transversely of the diaper.

DETAILED DESCRIPTION OF THE PREFERRED EMBODIMENTS

Details of a disposable diaper according to this invention will be more fully understood from the description given hereunder with reference to the accompanying drawings.

Figure 1:
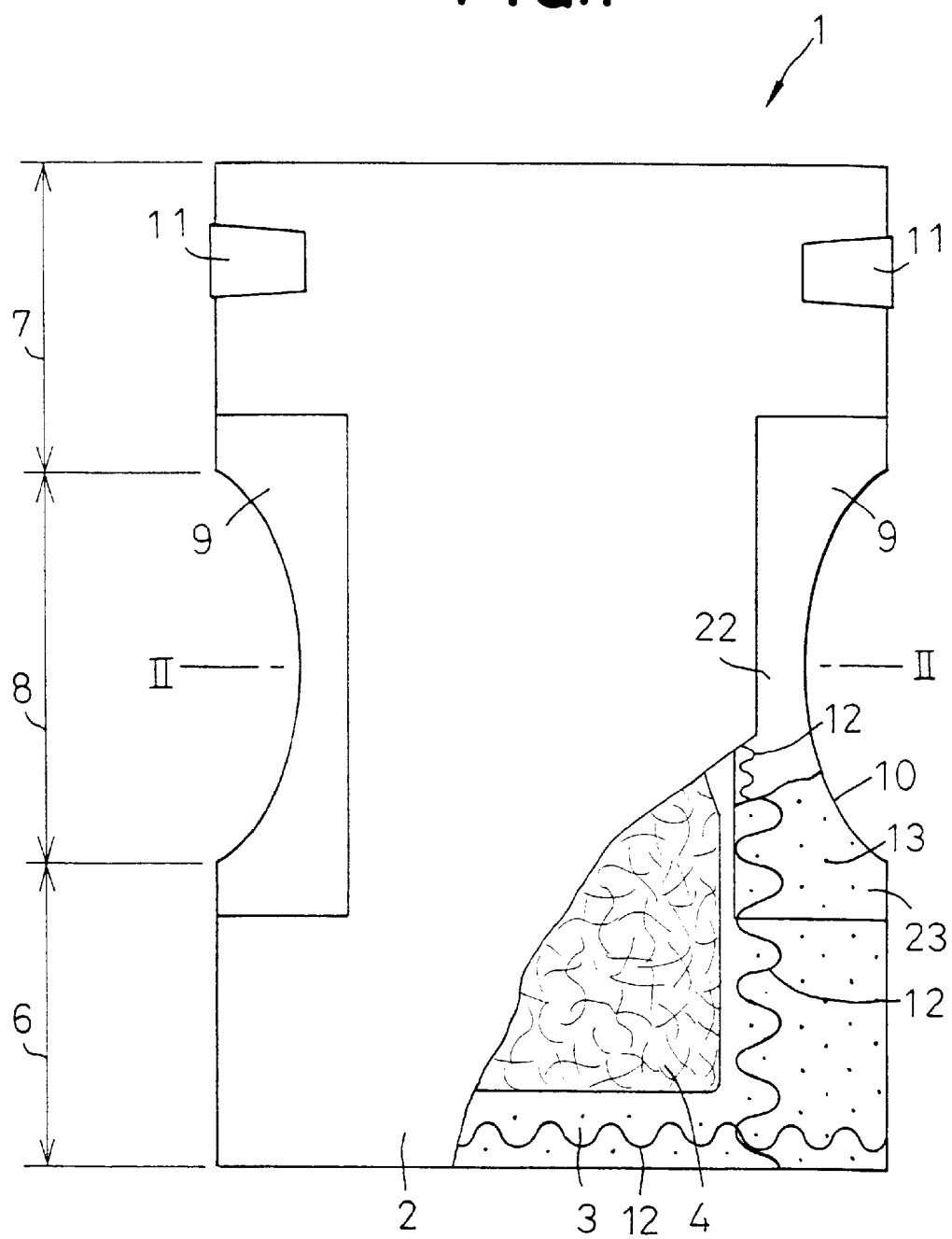
FIG. 1 is a partially cutaway plan view showing a disposable diaper according to a principle of this invention.
Figure 2:
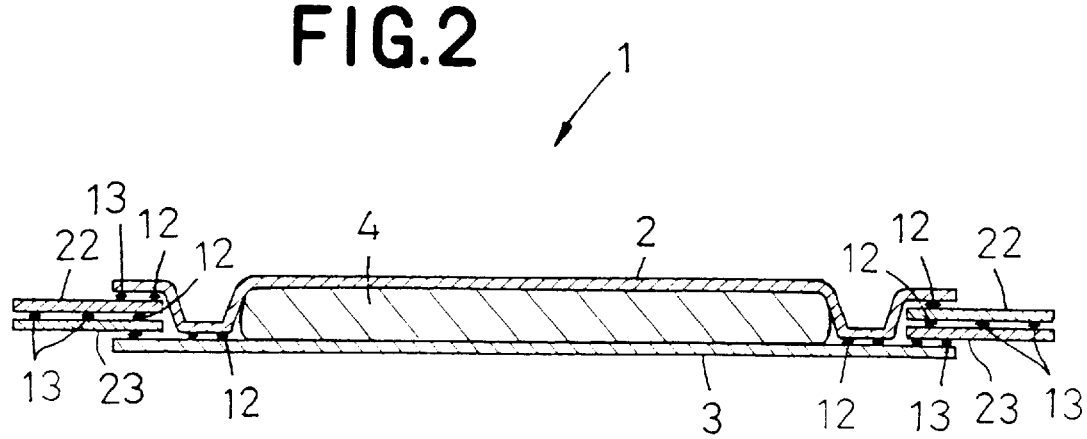
FIG. 2 is a sectional view taken along line II—II in FIG. 1.

FIG. 1 is a partially cutaway plan view showing a disposable diaper 1 and FIG. 2 is a sectional view taken along line II—II in FIG. 1. The diaper 1 comprises a liquid-previous topsheet 2 intended to come in contact with the wearer's skin, a liquid-impervious backsheet 3 intended to come in contact with the wearer's garment and a liquid-absorbent core 4 disposed between these two sheets 2, 3. Longitudinally, the diaper 1 has a front waist region 6, a rear waist region 7 and a crotch region 8 extending between these two waist regions 6, 7. The crotch region 8 has its transversely opposite side edges 9, 9 partially cut away to form curved edges 10, 10 adapted to fit around the wearer's legs. The rear waist region 7 is provided on its transversely opposite side edges with tape fasteners 11, 11, respectively. The top- and backsheets 2, 3 are placed upon and joined to each other by means of hot melt adhesive 12 along their portions extending outward beyond a peripheral edge of the core 4.

In such diaper 1, both the top- and backsheets 2, 3 are elastically stretchable in the transverse direction which is orthogonal to the longitudinal direction of the diaper 1. It should be understood here that, in the vicinity of the side edges 9, 9 of the crotch region 8, the top- and backsheets 2, 3 are partially cut away and these portions of the sheets 2, 3 thus cut away are replaced by separate top- and backsheets 22, 23 both associated with the leg-openings. These top- and backsheets 22, 23 are elastically stretchable longitudinally as well as transversely of the diaper 1. The topsheet 22 associated with the leg-openings is preferably sweat-absorbent and breathable while said backsheet 23 associated with the leg-openings is preferably breathable and liquid-impervious. These top- and backsheets 22, 23 are bonded to the respective inner surfaces of the top- and backsheet 2, 3, for example, by means of hot melt adhesive 12 applied thereon in a pattern of sine curves. The top- and backsheets 22, 23 associated with the leg-openings are also placed upon and joined to each other by means of hot melt adhesive 13 applied thereon in a pattern of sine curves or small dots (See FIG. 1).

The diaper 1 can be put on the wearer merely by unfolding it as seen in FIG. 1. This diaper 1 is free from the gathers as in the conventional diaper and therefore can be put on the wearer immediately after the diaper 1 has been unfolded without time and trouble taken to stretch the gathers. The top- and backsheets 2, 3 may be circumferentially stretched to put the diaper 1 on the wearer with a good fit. The diaper 1 put on the wearer does not obstruct a movement of baby's legs because the portion of diaper 1 extending around the wearer's legs is free to be stretched in all directions.

Figure 3:
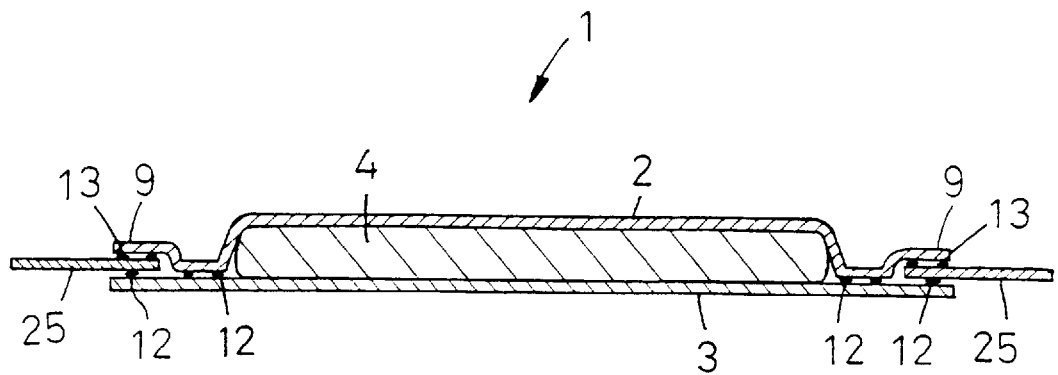
FIG. 3 is a view similar to FIG. 2 but showing another embodiment of this invention.

FIG. 3 is a view similar to FIG. 2 but showing another embodiment of this invention. According to this embodiment of diaper 1, the crotch region 8 is provided along each of its side edges 9 with a single sheet 25 associated with the leg-opening bonded to the respective inner surfaces of the top- and backsheets 2, 3 by means of hot melt adhesive 12, 13. This single sheet 25 associated with the leg-opening serves both as the top- and backsheets 22, 23 associated with the leg-openings in the embodiment shown in FIG. 2.

Figure 4:
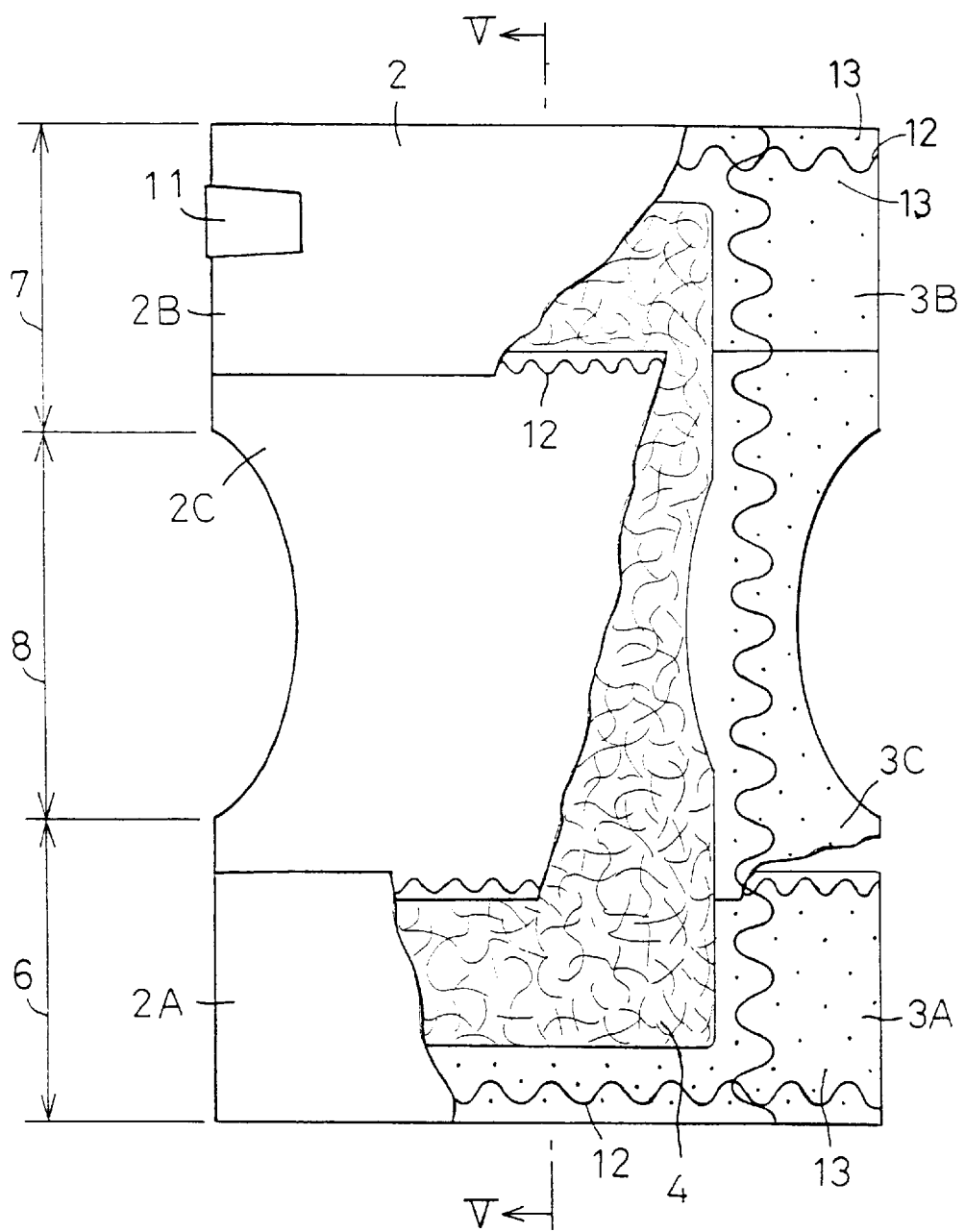
FIG. 4 is a view similar to FIG. 1 but showing still another embodiment of this invention.
Figure 5:
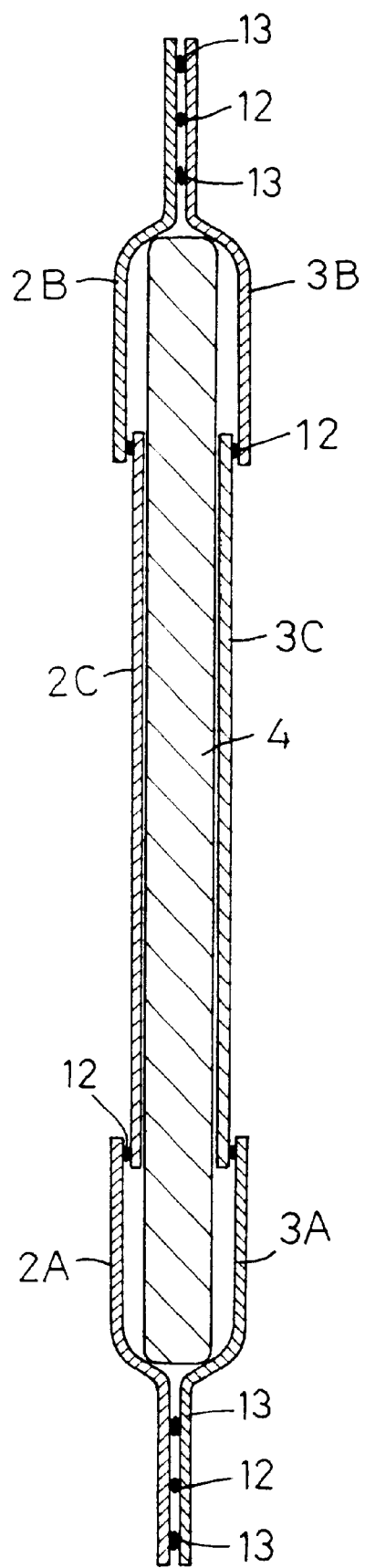
FIG. 5 is a sectional view taken along line V—V in FIG. 4.

FIGS. 4 and 5 are respectively a view similar to FIG. 1 but showing still another embodiment of this invention and a sectional view taken along line V—V in FIG. 4. According to this embodiment of diaper 1, the topsheet 2 is divided into topsheet sections 2A, 2B for the front and rear waist regions and a topsheet section 2C for the crotch region. Similarly, the backsheet 3 is divided into backsheet sections 3A, 3B and a backsheet section 3C for the crotch region. The topsheet sections 2A, 23 for the front and rear waist regions as well as the backsheet sections 3A, 3B for the front and rear waist regions are elastically stretchable transversely of the diaper 1. The topsheet sections 2C, 3C for the crotch region are elastically stretchable longitudinally as well as transversely of the diaper 1. These sheet sections 2A~2C and 3A~3C are bonded one to another along their overlapping zones by means of hot melt adhesive 12, 13 applied thereto in a pattern of sine curves or small dots. Referring to FIG. 5, the core 4 may be appropriately joined to the respective inner surfaces of the top- and backsheet sections 2A~2C and 3A~3C in the front and rear waist regions 6, 7 and in the crotch region 3. Similarly to the diaper 1 of FIG. 1, the diaper 1 according to this embodiment also can be easily put on the wearer and the diaper 1 having been put on the wearer does not obstruct a movement of the wearer legs as well as the wearer's crotch.

To make the diaper 1 according to this invention, a nonwoven fabric or an elastomer film having a monoaxial stretchability can be used as stock material for the top- and backsheets or their sections 2, 2A, 2B, 3, 3A, 3B. Such nonwoven fabric or elastomer may be formed with a plurality of pores each having an appropriate size to obtain a desired liquid-pervious property. A nonwoven fabric or an elastomer having a biaxial stretchability can be used as stock material for the top- and backsheet sections 22, 23 associated with the leg-openings, the single sheet 25 associated with each of the leg-openings and the top- and backsheet sections 2C, 3C of the crotch region. Bonding of such nonwoven fabric and film may be carried out using suitable adhesive agents such as hot melt adhesive or ultrasonic- or heat-sealing technique. It is important to perform operation of sheet-to-sheet bonding without deteriorating the original stretchability or these sheets. When adhesive agent is used, these sheets may be applied with adhesive agent in a pattern of sine curves to avoid an apprehensive deterioration of the sheets original stretchability and at the same time to prevent the body fluids from flowing between the top- and bakc-sheets 2, 3 from the core 4 toward the peripheral edge of the diaper 1.

What is claimed is:

1. A disposable diaper having a longitudinal direction and a transverse direction and comprising:

a topsheet;

a backsheet; and an absorbent core disposed between said topsheet and said backsheet, said diaper further having a front waist region, a rear waist region and a crotch region extending between said front and rear waist regions so that transversely opposite side edges of said crotch region surrounds a wearer's legs; and said topsheet and said backsheet being divided into topsheet and backsheet sections of said front and rear waist regions and of said crotch region, said topsheet and backsheet sections of said front and rear waist regions being elastically stretchable transversely of said diaper, said topsheet and backsheet sections of said crotch region being elastically stretchable in said longitudinal and transverse directions, said topsheet sections being overlapped and joined one to another in vicinities of boundaries of said front and rear waist regions and said crotch region, and said backsheet sections being also overlapped and joined one to another in vicinities of boundaries of said front and rear waist regions and said crotch region.

* * * * *